(12) United States Patent
Himmelsbach et al.

(10) Patent No.: US 6,544,910 B2
(45) Date of Patent: *Apr. 8, 2003

(54) BACKING MATERIAL FOR MEDICAL PURPOSES

(75) Inventors: Peter Himmelsbach, Buxtehude (DE); Stefan Bodenschatz, Buxtehude (DE)

(73) Assignee: Beiersdorf AG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/113,920

(22) Filed: Jul. 10, 1998

(65) Prior Publication Data

US 2001/0009828 A1 Jul. 26, 2001

(30) Foreign Application Priority Data

Jul. 12, 1997 (DE) ......................... 197 29 905

(51) Int. Cl.⁷ ................................................ A61F 13/00
(52) U.S. Cl. ................... 442/150; 442/5; 442/211; 442/313; 428/347; 428/902; 602/60
(58) Field of Search ................ 428/902, 292.1, 428/343, 347; 602/41–55, 60; 442/35, 36, 5, 211, 313, 150

(56) References Cited

U.S. PATENT DOCUMENTS

| 4,323,061 A | | 4/1982 | Usukura ..................... 128/90 |
| 4,668,563 A | | 5/1987 | Buese et al. ................ 428/230 |
| 4,756,942 A | | 7/1988 | Aichele ...................... 428/192 |
| 5,011,492 A | | 4/1991 | Heimerl et al. ............. 606/215 |
| 5,431,991 A | * | 7/1995 | Quantrille et al. .......... 428/109 |
| 5,453,319 A | * | 9/1995 | Gobran ....................... 428/355 |
| 5,938,631 A | * | 8/1999 | Colman ....................... 602/75 |
| 6,159,877 A | * | 12/2000 | Scholz et al. ............... 428/902 |

FOREIGN PATENT DOCUMENTS

| DE | 2641358 | 3/1977 | ........... A61L/15/06 |
| DE | 2728346 | 1/1978 | ............ C09J/7/02 |
| DE | G8336583.4 | 5/1985 | ............ C09J/7/02 |
| DE | 3433293 | 3/1986 | ............ C09J/7/02 |
| DE | 30809348 | 5/1989 | ........... A61F/13/02 |
| DE | 3805223 | 8/1989 | ............ G09F/3/10 |
| DE | 3929356 | 3/1990 | ........... A61F/13/00 |
| DE | 3915149 | 4/1991 | ........... C04B/35/71 |
| DE | 4033633 | 5/1991 | ............ D06N/7/00 |
| DE | 3940490 | 6/1991 | .......... C09J/201/02 |
| DE | 4239453 | 8/1993 | ........... A61L/15/07 |
| DE | 4215016 | 11/1993 | ........... D02G/3/46 |
| DE | 4237252 | 5/1994 | ............ C09J/7/02 |
| DE | 4308649 | 9/1994 | ........... A61L/15/42 |
| DE | 19531291 | 2/1997 | ............ A61K/9/70 |
| DE | 19620107 | 11/1997 | ............ C09J/7/04 |
| DE | 19628268 | 1/1998 | ............ C09J/7/04 |
| DE | 19628294 | 1/1998 | ........... A61F/13/02 |
| DE | 19631422 | 2/1998 | ............ C09J/7/02 |
| EP | 0341875 | 11/1989 | ............ D04H/1/56 |
| EP | 0353972 | 2/1990 | ........... A61F/13/02 |
| WO | 9515136 | 6/1995 | ........... A61F/13/02 |

* cited by examiner

Primary Examiner—Elizabeth M. Cole
(74) Attorney, Agent, or Firm—Norris, McLaughlin & Marcus

(57) ABSTRACT

Essentially inelastic backing material for medical purposes, characterized in that the backing material has an addition of high-strength fibers, multi-strand yarns, mixed multistrands or filaments having an ultimate tensile stress strength of at least 60 cN/tex, preferably from 80 to 500 cN/tex, the high-strength fibers, multi-strand yarns, mixed multistrands or filaments having a water absorption of less than 10%, preferably less than 5% and, with particular preference, less than 3% and the high-strength fibers, multi-strand yarns, mixed multistrands or threads giving the backing material an ultimate stress strength of at least 50 N/cm, preferably from 60 to 450 N/cm and, with particular preference, from 65 to 250 N/cm, and in that the backing material is coated at least partially on at least one side with a hotmelt adhesive composition.

33 Claims, 1 Drawing Sheet

BACKING MATERIAL FOR MEDICAL PURPOSES

DESCRIPTION

Figure 1:
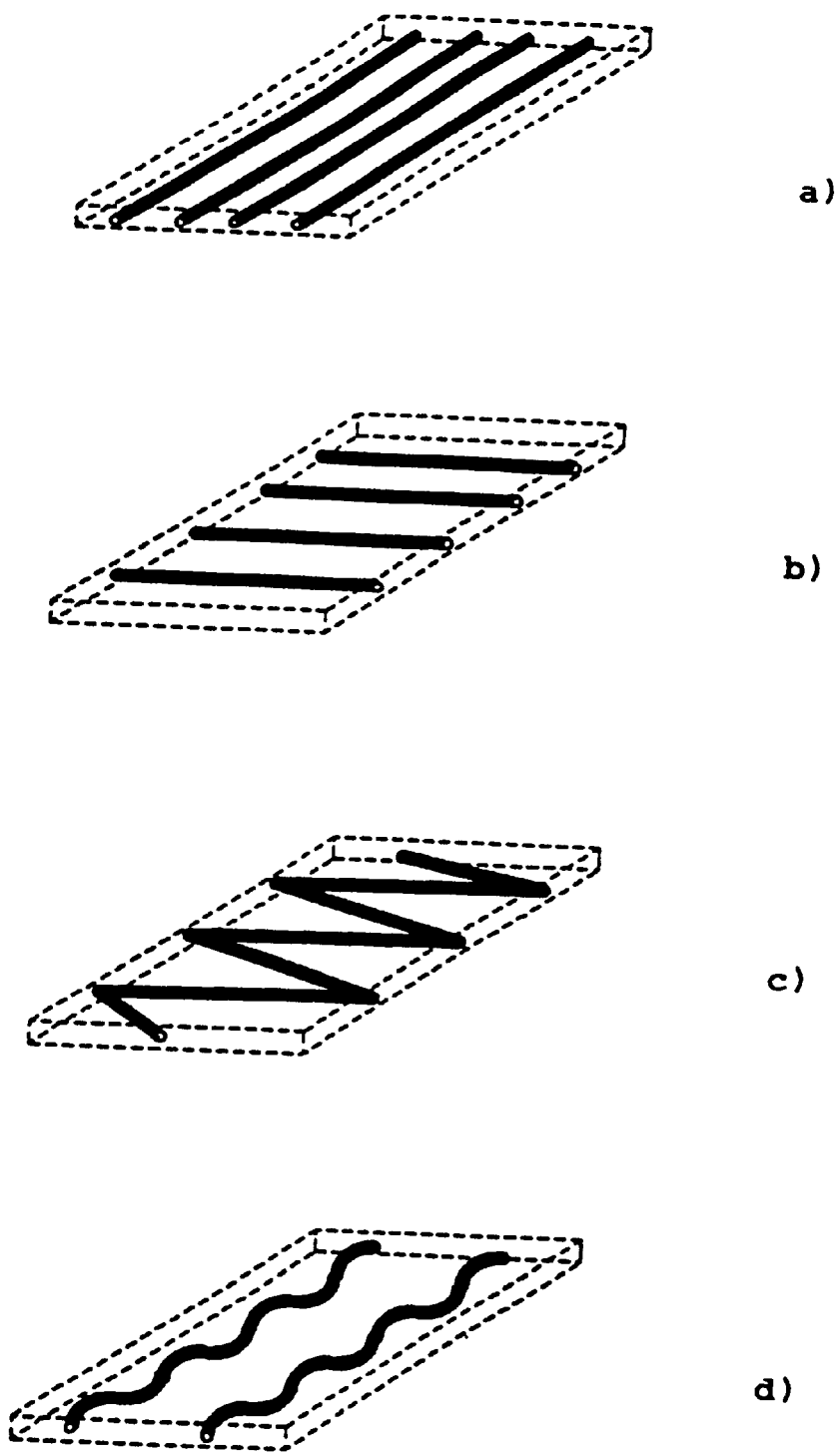

The invention relates to a backing material for medical purposes, preferably for orthopaedic dressings and bandages, which is coated on at least one side and at least partially with a hotmelt adhesive composition.

As backing materials for these purposes, numerous materials based on films, wovens, knits, nonwovens, gels or foams have already been disclosed and are also employed in practice. The materials, which are often coated with a self-adhesive composition as well, are required to be skin-compatible, generally permeable to air and water vapour, and also easy to model and conformable. Based on these requirements, a very thin or soft backing is frequently preferred. For handling and in use, however, the backing materials are also required to be of sufficient strength and possibly of limited extensibility. Furthermore, the backing material should retain sufficient strength and low extensibility even after becoming wet through.

Thin backings, especially those made of nonwovens, are highly permeable to air and water vapour. For certain applications, however, their strength is too low and their extension too high.

Specific applications, an example being tapes for functional tape dressings for the prophylaxis and therapy of injuries, disorders and altered states of the musculoskeletal system, require inelastic backings having high strength in the direction of stress. This is achieved by using woven fabrics, usually of cotton or viscose. Backing materials of this kind, with appropriately high basis weight, are generally cost-intensive. High flexibility can only be achieved by means of a woven fabric of relatively low strength. When such a fabric is stressed, however, it generally exhibits a certain degree of extension, which is undesirable for its use.

When these dressings become wet through, they generally lose strength or become more extensible. This is likewise undesirable for their use and has to date been compensated by more frequent changing of dressings, which, however, is cost-intensive.

Lamination with reinforcement threads has also been disclosed in the prior art by German Patent 571 244, although the reinforcement threads employed therein are not of high tenacity. The document, then, generally gives no indication of an inelastic backing.

In addition, AU 73555/74 describes by way of example a glass filament-reinforced backing material for medical application based on foam. The backing material described here, however, is elastic or at least plastically deformable.

U.S. Pat. No. 4,668,563 describes a glass fibre-reinforced material which, however, is elastic.

Furthermore, reinforcements are not unknown in the packaging sector.

Highly adhesive orthopaedic bandages and other medical products are usually coated over the whole of their area with a zinc-rubber adhesive composition. The sticking of such products to the skin entails, following their removal, marked skin irritation and mechanical stressing of the skin. Without recourse to auxiliary means, the bond cannot be detached without pain.

In some cases there are allergic reactions. Furthermore, the adhesive compositions used often lead to a transfer of composition onto the skin.

The use of skin-friendly adhesive compositions, such as acrylate adhesive compositions, is out of the question because of their low shear stability and finger tack. Improvement through aftertreatment, especially crosslinking, is possible, although the result remains unsatisfactory overall. In addition, the bond strength to the backing of such systems, in the case of multi-ply dressings applied in circular form, is inadequate for a stable functional dressing. The proprioreceptive effect is less than that of systems with a zinc-rubber adhesive composition.

Other known adhesive systems based on conventional block copolymers are not skin-friendly, owing to the high level of added stabilizer, or because of the high cohesiveness have been found suitable to date only for industrial application; or alternatively, they cannot be formulated for strong skin adhesion and sticking to the skin.

The abovementioned adhesive compositions are pressure-sensitive self-adhesive compositions, where the compositions may be present in a carrier matrix for the purpose of processing. The term carrier matrix is understood to refer to common inorganic or organic solvents or dispersion media.

Systems without a carrier matrix are referred to as 100% systems and are likewise not unknown. They are processed in the elastic or thermoplastic state. A common mode of processing is that of the melt.

Pressure-sensitive hotmelt adhesive compositions of this kind have also already been described in the prior art. They are based on natural or synthetic rubbers and/or other synthetic polymers.

Because of their high level of hardness, sticking to the skin is a problem for such 100% systems.

An advantage of 100% systems is that they avoid an operation of removing the carrier matrix, i.e. the auxiliary media, thereby raising the productivity of processing and at the same time reducing the expenditure on machinery and the energy costs. In addition, this reduces the occurrence of residues of the carrier matrix. This, in turn, favours a reduction in the allergenic potential.

It is also known to apply such self-adhesive compositions not only over the entire area but also in the form of a pattern of dots, for example by screen printing (DE P 42 37 252 C), in which case the dots of adhesive can also differ in their size and/or distribution (EP 0 353 972 B), or by intaglio printing, in lines which interconnect in the longitudinal and transverse direction (DE P 43 08 649 C).

The advantage of the patterned application is that the adhesive materials, given an appropriately porous backing material, are permeable to air and water vapour and, in general, are readily redetachable.

A disadvantage of these products, however, is that if the area covered by the adhesive film, which per se is impermeable, is too large there is a corresponding reduction in the permeability to air and water vapour, and the consumption of adhesive composition rises, and also, if the area covered by the adhesive film is too small, the adhesion properties suffer, i.e. the product is detached too readily from the substrate, especially in the case of heavy, textile backing materials.

The object of the invention, therefore, was to develop a backing material which meets the requirements of tensile strength and also elongation at break and durability and which, moreover, avoids the disadvantages of conventional adhesive systems as described in the prior art.

This object is achieved by adding high-strength fibres, multi-strand yarns, mixed multistrands or filaments—made of either an organic—or an inorganic-based material—having an ultimate tensile stress strength of at least 60 cN/tex, preferably from 80 to 500 cN/tex, to the essentially inelastic backing materials, the high-strength fibres, multi-strand yarns, mixed multistrands or filaments exhibiting a water absorption of less than 10%, preferably less than 5% and, with particular preference, less than 3%, and the high-strength fibres, multi-strand yarns, mixed multistrands or filaments giving the backing material an ultimate tensile stress strength of at least 50 N/cm, preferably from 60 to 450 N/cm and, with particular preference, from 65 to 250 N/cm.

In addition, the backing material is at least partially coated on at least one side with a pressure-sensitive hotmelt adhesive composition.

The backing material has preferably an extension of less than 10% at a load of 10 N/cm and also preferably a basis weight of less than 350 g/m$^2$, preferably less than 200 g/m$^2$.

Also preferably, the backing material has an ultimate tensile stress elongation of less than 25%, preferably less than 15% and, with particular preference, less than 10%.

The backing material may have been reinforced with one or more monofil, multifil, staple spun fibre yarns and/or with oriented high-strength fibres.

In addition it is also possible to employ multi-strand yarns or mixed multistrands, especially Sirospun yarns. For specific application, single- or multi-strand fibre blend yarns may also be employed. These may comprise, for example, core-spun yarns or special staple fibre core-spun yarns.

An advantage here is that combining high-strength reinforcements and base materials it is possible to achieve particular properties or specific properties in the reinforcement thread. Examples of this are the combinations of glass or carbon and cotton or staple viscose rayon.

The fibres or filaments here can consist of organic or inorganic materials: for example, and preferably, glass, carbon or specific polyamides, and the reinforcement fibres may also have been at least partly colored in order to render the backing material more visually appealing. In this way it is readily possible to differentiate visually the reinforced backing. Colored glass or polymer filaments are particularly suitable for this purpose.

Advantageously, the orientation of the reinforcement filaments or fibres is in accordance with the stress on the backing material in use.

The backing material is also preferably laminated with the filaments and/or high-strength fibres. The filaments and/or the high-strength fibres should be firmly connected to the backing material. This can be done by direct incorporation or embedding of the fibres, filaments or multi-strand yarns, including mixed multistrands, into the backing, such as by weaving them in in the case of wovens, knitting them in in the case of knits, or embedding or inserting them in the case of the preparation process of films, gels or foams and nonwovens.

Alternatively, the fibres or the high-strength filaments can be connected to the backing subsequently, examples being welding or lamination with a corresponding connecting layer. One method appropriate for this purpose is to lay them into the film of adhesive composition.

In one advantageous embodiment the backing material attains through the addition of high-strength fibres or filaments an ultimate tensile stress strength of more than 60 cN/tex, an ultimate tensile stress strength of more than 50 N/cm and an ultimate tensile stress elongation of less than 25% with a basis weight of less than 140 g/m$^2$. A backing material of this kind is particularly suitable for acting as the backing for a tape strip.

Preferably, in addition, at a load of 30N/cm the backing material can after 50 cycles be deformed by less than 20%, preferably 10% and, with particular preference, less than 5%.

Preferably, in addition, the backing material can be torn by hand perpendicular to the orientation of the reinforcement and/or in the direction of the reinforcement.

In addition, the backing material may also have been pretreated.

The number of attached or introduced filaments or high-strength fibres depends primarily on the particular intended use and on the desired ultimate tensile stress strength and ultimate tensile stress elongation of the backing material, on its inherent nature and on the respective strength of the fibres and filaments themselves, and can therefore be varied within relatively wide limits.

With increasing reinforcement, the backing withstands greater stress and loading. Even very highly reinforced backing materials are able to absorb or allow the passage of large amounts of moisture, and hence provide a pleasant sensation to the user.

In addition, the reinforcements are preferably inserted specifically in accordance with the direction of stress of the backing material, i.e. in the longitudinal direction. If more appropriate, however, they can also extend only or additionally in the transverse or oblique direction or, for example, in curved, spiral or zigzag formation, or randomly. In this context it may be desirable and possible to provide for the backing material to be tearable by hand perpendicular to the orientation of the reinforcement and/or in the direction of the orientation.

FIGS. 1$a$–$d$ shows by way of example various possible arrangements of the reinforcement threads in longitudinal, transverse, zigzag and wavy form.

In the case of ready-made tapes dressings the reinforcement filaments or fibres are preferably arranged equally in accordance with the direction of stress in the applied state. Since these dressings have already been cut to size or punched out, tearability is not a requirement here.

As backing material for a functional tape dressing it is possible, for example, to use a flexible woven cotton backing fabric to which carbon or glass fibre filaments have been added in the warp. For instance, every 2nd to 12th warp thread may consist of the high-strength material. By virtue of this construction the backing remains flexible and can be modelled on readily. At the same time it has a high tear strength, and its extensibility in the direction of stress is markedly reduced. Owing to the brittleness of the high-strength filaments, the fabric remains tearable by hand.

A backing of this kind which is suitable for tapes has, for example, an ultimate tensile stress strength of 65 N/cm and an ultimate tensile stress elongation of less than 10% for a basis weight of 200 g/m$^2$.

In another possible embodiment, the woven fabric consists of 100% high-strength materials in the warp and gives tape backings having particularly high ultimate tensile stress strength (>250 N/cm) and low ultimate stress elongation (<5%). Such a backing is used for particularly high loads and stresses in the tape sector.

Durability was found to be particularly advantageous in the cyclical long-term stress test. Here it was found that, even at a low load of about 30 N/cm and with few cycles, the extension of a customary commercial backing material is about twice as high as that of a backing material reinforced with high-strength fibres or filaments. In some cases, the extension was seven to eight times higher than that of the reinforced backing materials, although the ultimate tensile stress strength of the backing materials was comparable.

Following a long-term stress loading of 50 cycles, a backing according to the invention, depending on its material composition, has a deformation in the direction of load of less than 20%, preferably less than 10% and, with particular preference, less than 5%.

For the backing material of the invention for medical purposes it is preferable, moreover, to use a pressure-sensitive hotmelt adhesive composition which has a dynamic-complex glass transition temperature at a frequency of 0.1 rad/s of less than 5° C., preferably from −6° C. to −30° C. and, with particular preference, from −9° C. to −25° C.

The hotmelt adhesive composition in this case can be built up on a base of block copolymer, especially A-B or A-B-A block copolymers or mixtures thereof, phase A principally being polystyrene or its derivatives and phase B ethylene, propylene, butylene, butadiene, isoprene or mixtures thereof, with particular preference ethylene and butylene or mixtures thereof. Polystyrene blocks, however, may also be present in phase B in amounts of up to 20%.

The controlled blending of diblock and triblock copolymers is particularly advantageous, preference being given to a proportion of diblock copolymers of less than 80% by weight.

The overall proportion of styrene in the polymer should preferably be less than 35% by weight, preferably from 5% to 30% by weight. A relatively low proportion of styrene makes the hotmelt pressure-sensitive adhesive composition more conformable.

In one advantageous embodiment the hotmelt adhesive composition is composed as follows:
- from 10 to 90% by weight of block copolymers,
- from 5 to 80% by weight of tackifiers such as oils, waxes, resins and mixtures thereof, preferably mixtures of resins and oils, the oils, waxes and resins employed preferably being hydrocarbon oils, hydrocarbon waxes and hydrocarbon resins,
- less than 60% by weight of plasticizers,
- less than 15% by weight of additives, and
- less than 5% by weight of stabilizers.

The hydrocarbon oils (for example, paraffinic hydrocarbon oils), waxes and resins which are preferably used serve as tackifiers, and through their consistency have a favourable effect on bonding to the skin.

Plasticizers used are long-chain fatty acids and/or their esters. These additives serve to establish the adhesion properties and the stability.

The hotmelt adhesive composition has a softening point of more than 70° C., preferably from 85 to 140° C.

Preferably in addition the hotmelt adhesive composition is applied to the backing material by halftone printing, thermal screen printing or intaglio printing and moreover, in a particularly preferred embodiment, is applied in the form of polygeometric domes.

The percentage proportion of the surface that is coated with the hotmelt adhesive composition should in the case of partial coating of the backing material be at least 20% and can range up to about 95%, for specific products preferably from 40 to 60% and from 70 to 95%. This can if required be achieved by multiple application, it also being possible if desired to employ hotmelt adhesive compositions having different properties.

With further preference, the hotmelt adhesive composition is coated onto the backing material with a weight per unit area of greater than 15 g/m$^2$, preferably between 70 and 300 g/m$^2$ and, with very particular preference, between 90 and 160 g/m$^2$.

Preferably as well the coated backing material has an air permeability of greater than 1 cm$^3$/(cm$^2$*s), preferably greater than 15 cm$^3$/(cm$^2$*s) and, with very particular preference, greater than 70 cm$^3$/(cm$^2$*s), and/or a water vapour permeability of greater than 500 g/(m$^{2*24}$h), preferably greater than 1000 g/(m$^{2*24}$h), and, with particular preference, greater than 2000 g/(m$^{2*24}$h).

In addition, non-tacky substances, such as mineral fillers, for example, can be mixed in with the hotmelt adhesive composition.

The backing material which has been rendered self-adhesive by means of the hotmelt adhesive composition also preferably has, in the case of bonding to steel and on the reverse of the backing, a bond strength of at least 1.5 N/cm, in particular a bond strength of between 2.5 and 5 N/cm. Higher bond strengths may be achieved on other substrates.

Stringent requirements are placed in terms of the adhesion properties on medical products in particular, for example an orthopaedic dressing. For ideal use the hotmelt adhesive composition should possess a high tack. There should be functionally appropriate bond strength to the skin and to the reverse of the backing. So that there is no slipping of the plies, the hotmelt adhesive composition is also required to have a high shear strength.

By the controlled reduction in the glass transition temperature of the hotmelt adhesive composition, which is a result of the selection of the tackifiers, the plasticizers, the polymer molecule size and the molecular distribution of the starting components, the required, functionally appropriate bonding to the skin and to the reverse of the backing is achieved.

The high shear strength of the hotmelt adhesive composition which is employed here is obtained by virtue of the high cohesiveness of the block copolymer. The good tack is the result of the range of tackifiers and plasticizers employed.

Product properties such as tack, glass transition temperature and shear stability can be quantified readily using a dynamo-mechanical frequency measurement. In this case, use is made of a rheometer controlled by shearing stress. Rheometers of this kind are known.

The results of this measurement method give information of the physical properties of a substance by taking into account the viscoelastic component. In this instance, at a predetermined temperature, the hotmelt adhesive is set in oscillation between two plane-parallel plates at variable frequencies and with low deformation (linear viscoelastic region). Via a pickup control unit, with computer assistance, the quotient (Q=tan δ) between the loss modulus (G", viscous component) and the storage modulus (G', elastic component) is determined. A high frequency is chosen for the subjective sensing of the tack, and a low frequency for the shear strength.

A high numerical value denotes better tack and poorer shear stability.

The complex-dynamic glass transition point is the point of transition from the amorphous to the viscoelastic region. It corresponds to the maximum of the temperature function at a given frequency.

$$Q=\tan \delta = G"/G'$$

| Designation | $T_g$ low frequency | Shear stability low frequency/ RT | Tack high frequency/ RT |
|---|---|---|---|
| Hotmelt adhesive A | $-12 \pm 2°$ C. | tan δ = 0.18 ± 0.03 | tan δ = 0.84 ± 0.03 |
| Hotmelt adhesive B | $-9 \pm 2°$ C. | tan δ = 0.29 ± 0.05 | tan δ = 1.70 ± 0.10 |

Preference is given in accordance with the invention to hotmelt adhesive compositions for which the ratio of the loss modulus (viscous component) to the storage modulus (elastic component) at a frequency of 100 rad/s and at 25° C. is greater than 0.7, preferably from 0.9 to 4.5, or to hotmelt adhesive compositions for which the ratio of the viscous component to the elastic component at a frequency of 0.1 rad/s at 25° C. is less than 0.40, preferably from 0.35 to 0.02 and, with particular preference, between 0.30 and 0.10.

It is also advantageous, especially with use for medical products, if the hotmelt adhesive composition is applied partially to the backing material, for example by means of halftone printing, thermal screen printing or intaglio printing, because backing materials which have been self-adhesively treated in a continuous applied line may, on application, induce mechanical irritations of the skin.

The partial application makes it possible to dissipate the trans-epidermal water loss through controlled channels and improves the removal of sweat from the skin in vapour form, especially when the backing materials used are permeable to air and water vapour. By this means the skin irritations induced by cumulations of body fluids are avoided. The dissipation channels set up enable fluids to be conducted away even when a multi-ply dressing is used.

Where partial application of the hotmelt adhesive composition is by thermal screen printing, the web-to-hole ratio of the screen can be less than 2:1, preferably less than or equal to 1:1.

The principle of thermal screen printing consists in the use of a rotating, heated, seamless, drum-shaped, perforated, cylindrical screen which is fed via a nozzle with the hotmelt adhesive composition. A specially shaped nozzle lip (circular or square bar) presses the self-adhesive composition, which is fed in via a channel, through the perforation of the screen wall and onto the backing web that is conveyed past it. This web is guided by means of a counterpressure roller against the external jacket of the heated screen drum at a rate which corresponds to the peripheral speed of the rotating screen drum.

As already stated above, preference is given to application in the form of domes, and especially those domes where the ratio of diameter to height is less than 5:1. Printed application of other forms and patterns on the backing material is also possible; for example, a printed pattern in the form of alphanumeric character combinations or patterns such as matrices, stripes and zigzag lines.

In this context, the formation of the small domes of adhesive takes place by the following mechanism:

The pressure of the nozzle bar conveys the self-adhesive composition through the screen perforation onto the backing material. The size of the domes formed is determined by the diameter of the screen perforation. The screen is lifted from the backing in accordance with the rate of transportation of the backing web (rotary speed of the screen drum). As a consequence of the high adhesion of the self-adhesive composition and the internal cohesion of the hotmelt, the limited supply of hotmelt adhesive composition in the perforations is drawn in sharp definition from the base of the dome that is already adhering to the backing and is conveyed by the pressure of the bar onto the backing.

After the end of this transportation, the more or less strongly curved surface of the dome forms over the pre-defined base area in dependence on the rheology of the hotmelt adhesive composition. The height-to-base ratio of the dome depends on the ratio of the perforation diameter to the wall thickness of the screen drum and on the physical properties (flow behaviour, surface tension and contact angle on the backing material) of the self-adhesive composition.

The above-described mechanism of formation of the domes preferentially requires backing materials that are absorbent or at least wettable by hotmelt adhesive compositions. Non-wetting backing surfaces must be pretreated by chemical or physical techniques. This can be effected by additional measures such as corona discharge, for example, or by coating with substances which improve wetting.

Using the printing technique indicated it is possible to lay down the size and shape of the domes in a defined manner. The bond strength values which are relevant for use and which determine the quality of the products formed are within very narrow tolerances in the case of proper coating. The base diameter of the domes can be chosen from 10 to 5000 μm, the height of the domes from 20 to about 2000 μm, preferably from 50 to 1000 μm the low-diameter range being intended for smooth backings and the range of greater diameter and greater dome height being intended for rough or highly porous backing materials.

The positioning of the domes on the backing is laid down in a defined manner by the geometry of the applicator unit, for example the gravure or screen geometry, which can be varied within wide limits. With the aid of the parameters indicated it is possible, by way of adjustable variables, to establish with very great precision the desired profile of properties of the coating, harmonized with various backing materials and applications.

The backing material is preferably coated at a rate of more than 2 m/min, preferably from 20 to 100 m/min, the chosen coating temperature being greater than the softening temperature.

In addition, the hotmelt adhesive composition can also, for example, be sprayed on, giving a more or less irregular pattern of application.

The hotmelt adhesive composition can be distributed uniformly on the backing material, or else can be applied in varying thickness or density as appropriate to the functioning of the product.

The combination of the hotmelt adhesive composition and the partial coating on the one hand ensures reliable bonding of the medical product to the skin and, on the other hand, allergic or mechanical skin irritations, at least which are visually perceptible, are ruled out, even in the case of use extending over a number of days.

The epilation of corresponding body regions and the transfer of composition to the skin are negligible owing to the high cohesiveness of the adhesive, since the adhesive does not attach to the skin and hair. The anchorage of the hotmelt adhesive composition to the backing material, moreover, at up to 12 N/cm (sample width), is good for medical applications.

Because of the intended breakage points that have been formed in the partial coating, layers of skin are no longer displaced with one another or against one another in the course of detachment. The non-displacement of these layers of skin and the relatively low level of epilation lead to an unprecedented degree of painlessness in such strongly adhering systems. In addition, the individual biomechanical control of bond strength, which exhibits a demonstrable reduction in the bond strength of these self-adhesively treated backing materials, assists detachability. The applied dressing shows good proprioreceptive effect.

Depending on the backing material and its temperature sensitivity, the hotmelt adhesive film can be applied directly or can be applied first to an auxiliary support and then to the ultimate backing. In addition, subsequent calendering of the coated product and/or pretreatment of the backing, such as corona irradiation, may be advantagous for better anchorage of the adhesive film.

For medical application, moreover, the self-adhesively treated backing material according to the invention is preferably covered after application or provided with a wound pad or with padding.

Furthermore, the self-adhesively treated backing material can be sterilizable, preferably with γ (gamma) radiation.

The outstanding properties of the self-adhesively treated backing material according to the invention suggest its use for medical products, especially plasters, medical fixings, wound covers and also orthopaedic or phlebological bandages and dressings.

Advantageously it has been found that a reinforced backing material with such a self-adhesive coating, on becoming wet through—as is unavoidable, for example, in the course of water sports activities—has a stability which is better than that of customary commercial backing material. The relative increase in the ultimate tensile stress elongation of self-adhesively treated backing materials according to the invention after becoming wet through is only half as great as in the case of customary commercial self-adhesively treated backing materials.

By virtue of this the backing materials of the invention, which indeed are thus essentially inelastic, become useful for specific medical purposes, and it is also possible to employ backing materials whose use hitherto was impossible owing to lack of strength and/or excessive elongation.

With preference it is possible to use backing materials based on wovens, knits, nonwovens or composite products, provided they otherwise meet the requirements of medical use.

EXAMPLE

The text below describes by way of example a preferred backing material, without thereby wishing to restrict the invention unnecessarily.

The thread constellation of the backing material was 30 threads in the warp direction and 28 threads in the lengthwise direction. Every 12th warp thread was replaced by a glass fibre reinforcement thread. The remaining warp and weft threads consisted of cotton. The threads in this arrangement were selected so as not to differ significantly in thickness.

The production of such backing materials is known in the art and can take place, for example, by using two warp beams or by causing the reinforcement threads to run together from a creel. Subsequently, the backing material can be finished using a wide variety of steps. Examples are textile technologies such as desizing, singeing, calendering, stretching, colouring, hydrophobicizing, etc.

The resulting backing material had an ultimate tensile stress strength of about 90 N/cm and an ultimate tensile stress elongation of 8% in the lengthwise direction. The basis weight was approximately 120 g/cm$^2$. After being wet through completely, the backing material had an ultimate stress strength of 85 N/cm. The ultimate tensile stress elongation was 12%.

The backing material had an air permeability of 100 cm$^3$/(cm$^{2*}$s) and a water vapour permeability of greater than 2500 g/(M$^{2*24}$h) and could be torn both partly and right through by hand in both crosswise and lengthwise directions.

Overall, the backing material in the soaked-through state could be extended less than comparable backings which consisted only of cotton.

The hotmelt adhesive composition was composed as follows:

an A-B/A-B-A block copolymer, which consists of hard and soft segments, with a ratio of A-B-A to A-B of 2:1 and a styrene content in the polymer of 13 mol-%; its proportion in the adhesive composition is 40% by weight (Kraton G), a paraffinic hydrocarbon resin with a proportion in the adhesive composition of 55% by weight, hydrocarbon resins with a proportion of 4.5% by weight (Super Resin HC 140), an ageing inhibitor with a proportion of less than 0.5% by weight (Irganox 1010).

The components employed were homogenized in a thermal mixer at 175° C.

The softening point of this adhesive composition was about 85° C. (DIN 52011) and it had a viscosity of 2100 mPas at 175° C. (DIN 53018, Brookfield DV II, sp. 21). The glass transition by the abovementioned method was −9° C.

The hotmelt adhesive composition was applied to the backing by thermal screen printing. Direct coating took place at 50 m/min and at a temperature of 120° C. The backing material was partially coated with 120 g/m$^2$ using a 14 mesh screen with a thickness of 300 μm.

The bandage produced by this method exhibited reversible detachment from the skin and good permeability for air and water vapour. Owing to the high shear stability of the hotmelt pressure-sensitive adhesive, sufficient stabilization and a good proprioreceptive effect were found. No skin irritations were observed, and the epilation observed following the removal of the bandage was negligible.

What is claimed is:

1. An essentially inelastic backing material for medical purposes, comprising:

a layer of woven or knitted cotton or viscose comprising warp threads and weft threads;

threads of high-strength fibers, multi-strand yarns, mixed multistrands or filaments, having an ultimate tensile stress strength of at least 60 cN/tex and a water absorption of less than 10%, incorporated into the weave or knit as warp threads or weft threads or both; said layer of cotton or viscose with said fibers, yarns, multistrands or filaments incorporated therein having an ultimate tensile stress strength of at least 50 N/cm;

wherein the backing material is coated at least partially on at least one side with a hotmelt adhesive.

2. Backing material for medical purposes according to claim 1, wherein the backing material has an elongation of less than 10% at a load of 10 N/cm.

3. Backing material for medical purposes according to claim 1 wherein the backing material has a basis weight of less than 350 g/m$^2$, preferably less than 200 g/m$^2$.

4. Backing material for medical purposes according to claim 1, wherein the backing material has an ultimate tensile stress elongation of less than 25%, preferably less than 15% and, with particular preference, less than 10%.

5. Backing material for medical purposes according to claim 1, wherein the backing material is reinforced with one or more monofil, multifil, staple or spun fibre yarns and/or with oriented high-strength fibres.

6. Backing material for medical purposes according to claim 1, wherein the backing material is laminated with the yarns and/or high-strength fibres.

7. Backing material according to claim 1, wherein the yarns, high-strength fibers, or both are embedded into the backing material.

8. Backing material according to claim 1, wherein through the addition of high-strength fibers or yarns of a material having an ultimate tensile stress strength of more than 60 cN/tex the backing material has an ultimate tensile stress strength of more than 65 N/cm and an ultimate tensile stress elongation of less than 25% at a basis weight of less than 140 g/m$^2$.

9. Backing material according to claim 1, wherein the backing material is deformed by less than 20% after 50 cycles at a load of 30 N/cm.

10. Backing material according to claim 1, wherein the backing material is tearable by hand perpendicular to the orientation of the reinforcement or in the direction of the reinforcement or both.

11. Backing material according to claim 1, wherein the hotmelt adhesive composition has a dynamic-complex glass transition temperature at a frequency of 0.1 rad/s of less than 5° C.

12. Backing material according to claim 1, wherein the ratio of the loss modulus (viscous component) to the storage modulus (elastic component) of the hotmelt adhesive composition at a frequency of 100 rad/s at 25° C. is greater than 0.7.

13. Backing material according to claim 1, wherein the ratio of the loss modulus (viscous component) to the storage modulus (elastic component) of the hotmelt adhesive composition at a frequency of 0.1 rad/s at 25° C. is less than 0.40.

14. Backing material according to claim 1, wherein the hotmelt adhesive composition is based on block copolymers.

15. The backing material of claim 14, wherein said block copolymers are A-B block copolymers, A-B-A block copolymers or a mixture thereof, wherein phase A is principally polystyrene or a derivative thereof, and phase B is ethylene, propylene, butylene, butadiene, isoprene or a mixture thereof.

16. Backing material for medical purposes according to claim 1, wherein the hotmelt adhesive composition consists of from 10 to 90% by weight of block copolymers,
from 5 to 80% by weight of tackifiers
less than 60% by weight of plasticizers,
less than 15% by weight of additives, and
less than 5% by weight of stabilizers.

17. Backing material according to claim 1, wherein the hotmelt adhesive composition is applied by halftone printing, thermal screen printing or intaglio printing.

18. Backing material according to claim 12, wherein the hotmelt adhesive composition is applied in the form of polygeometric domes to the backing material.

19. Backing material according to claim 12, wherein the hotmelt adhesive composition is coated on the backing material with a weight per unit of greater than 15 g/m$^2$.

20. Backing material according to claim 12, wherein the coated backing material has an air permeability of greater than 1 cm$^3$/(cm$^2$*s) and a water vapor permeability of greater than 500 g/(m$^2$*24 h).

21. Backing material according to claim 1, wherein the self-adhesively treated backing material is covered after application or is provided with a wound pad or with padding.

22. Backing material for medical purposes according to claim 1, wherein the self-adhesively treated backing material is sterilizable with γ (gamma) radiation.

23. Medical products selected from the group consisting of plasters, medical fixings, wound covers, orthopaedic, phiebological bandages, and dressings comprising a backing material according to claim 1.

24. The backing material of claim 1, wherein said water absorption is less than 3%, and said ultimate stress strength is 65 to 250 N/cm.

25. The backing material of claim 3, wherein said basis weight is less than 200 g/m$^2$.

26. The backing material of claim 4, wherein said ultimate tensile stress elongation is less than 10%.

27. The backing material of claim 9, wherein said backing material is deformed less than 5%.

28. The backing material of claim 11, wherein said ratio of the loss modulus to the storage modulus is from 0.9 to 4.5.

29. The backing material of claim 13, wherein said ratio of the loss modulus to the storage modulus is between 0.30 and 0.10.

30. Backing material for medical purposes according to claim 15, wherein the overall styrene content in the polymer is less than 35% by weight.

31. The backing material of claim 15, wherein phase B is ethylene, butylene or a mixture thereof.

32. Backing material according to claim 19, wherein said weight per unit is between 90 g/m$^2$ and 160 g/m$^2$s.

33. Backing material according to claim 20, wherein said air permeability is greater than 70 cm$^3$/cm$^2$*s) and said water vapor permeability is greater than 2000 g/m$^2$*24H).

* * * * *

UNITED STATES PATENT AND TRADEMARK OFFICE
CERTIFICATE OF CORRECTION

PATENT NO. : 6,544,910 B2
APPLICATION NO. : 09/113920
DATED : April 8, 2003
INVENTOR(S) : P. Himmelsbach et al.

It is certified that error appears in the above-identified patent and that said Letters Patent is hereby corrected as shown below:

Column 11, Line 52, "tackifiers" should read -- tackifiers, --

Column 12, Line 25, "phiebological" should read -- phlebological --

Column 12, Line 47, "160 g/m²s." should read -- 160 g/m². --

Signed and Sealed this

Thirty-first Day of July, 2007

JON W. DUDAS
*Director of the United States Patent and Trademark Office*